United States Patent [19]

Shinitzky et al.

[11] 4,071,770

[45] Jan. 31, 1978

[54] METHOD FOR EVALUATING PERINATAL LUNG MATURITY

[75] Inventors: Meir Shinitzky, Rehovot; Abraham Bruck, Haifa, both of Israel

[73] Assignee: Elscint, Ltd., Haifa, Israel

[21] Appl. No.: 676,798

[22] Filed: Apr. 14, 1976

[30] Foreign Application Priority Data

Mar. 2, 1976 Israel .................................. 49130

[51] Int. Cl.² ........................................... G01N 21/38
[52] U.S. Cl. ................................. 250/461 B; 250/302
[58] Field of Search ........................... 250/461 B, 302

[56] References Cited

U.S. PATENT DOCUMENTS

| | | | |
|---|---|---|---|
| 3,883,247 | 5/1975 | Adams | 250/461 B |
| 3,887,812 | 6/1975 | Hirschfeld | 250/461 B |
| 3,971,952 | 7/1976 | Inbar et al. | 250/461 B |

*Primary Examiner*—Archie R. Borchelt

*Attorney, Agent, or Firm*—Donald M. Sandler

[57] ABSTRACT

Perinatal lung maturity is evaluated by determining the fluorescence polarization of a sample of pulmonary effluent containing pulmonary surfactant labeled with a fluorescent dye. The sample is excited with polarized radiation for causing the dye to fluoresce. $I_\parallel$ and $I_\perp$, the intensities of fluorescence polarized in directions parallel to, and perpendicular to, the direction of polarization of the excitation radiation, are measured. From these measurements, the fluorescence polarization P, where $P = (I_\parallel - I_\perp)/(I_\parallel + I_\perp)$, is determined. The value of P, which is functionally related to the microviscosity of the constituents of the surfactant, has been found to decrease with perinatal lung maturity. When the sample is amniotic fluid containing fetal pulmonary effluent, the evaluation of lung maturity can be carried out antepartum. Postpartum evaluation can be carried out by sampling neonatal tracheal or pharyngeal aspirates.

9 Claims, No Drawings

4,071,770

METHOD FOR EVALUATING PERINATAL LUNG MATURITY

CROSS-REFERENCE TO RELATED APPLICATION AND ARTICLES

The following articles are referred to in the specification:
1. Blumenfeld, T. A. "Clinical Laboratory Tests for Fetal Lung Maturity". Pathology Annual 1975, Pages 21–36.
2. Blumenfeld, T. A.; Driscoll, J. M.; and James, L. S., "Lecithin/Sphingomyelin Ratios in Tracheal and Pharyngeal Aspriates in RDS". J. Pediatrics, Vol. 85, No. 3, pages 403–407 (1974).
3. Shinitzky, M.; Dianoux, A. C.; Gitler, C; and Weber, G. Biochemistry, Vol. 10, pages 2106–2113 (1971).
4. Teichberg, V. I. and Shinitzky, M. J. Mol. Biol. Vol. 74, pages 519–531.
5. Shinitzky, M. and Barenholz, Y. J. Biol. Chem., Vol. 249, No. 8, pages 2652–2657 (1974).

BACKGROUND OF THE INVENTION

This invention relates to a method for evaluating perinatal lung maturity.

Respiratory distress syndrome (RDS), which each year claims the lives of thousands of newborn, is a disease caused by a deficiency in pulmonary surfactant, a substance that reduces alveolar surface tension. The fetal lung produces surfactant that reaches the amniotic fluid; and it is known that at approximately 35 weeks gestation, the surfactant, predominantly dipalmitoyl lecithin, increases substantially. The relative or absolute quantity of this substance in amniotic fluid is conventionally used as a measure of lung maturity to evaluate the probability of survival after delivery.

Three laboratory tests for lecithin are presently in wide use: the ratio of lecithin (L) to sphingomyelin (S), often referred to as the L/S ratio; the bubble stability or shake test; and the determination of surface tension.

It has been confirmed experimentally, that an L/S ratio of two or more in amniotic fluid is indicative of lung maturity. If a fetus is delivered after this ratio is achieved, RDS generally does not occur. This test is well known and widely used, particularly when the fetus is to be delivered by Caesarian section and the degree of lung maturity must be established beforehand. In such case, a sample of amniotic fluid is taken, and within an hour or so, the L/S ratio can be determined. Reference (1) discusses 19 different techniques presently used for carrying out this test.

The bubble stability test, which is qualitative, is quicker and less complicated. It involves a shaking a mixture of amniotic fluid in ethanol to determine whether a stable foam is generated. The stability of the foam is considered to result from the presence of the surfactant since this lowers the surface tension of the fluid. This test is useful as a rapid screening procedure for fetal lung maturity because experience shows that a positive test is indicative of pulmonary maturity. Because of the high incidence of false negative results, however, a negative test is usually interpreted as indicating a more quantitative test must be carried out.

The lecithin concentration in amniotic fluid may be determined by various chemical processes or by chromatography apparatus. While this measurement should be superior to others that only indirectly measure lecithin, it is more time consuming by a factor of two or three as compared to determining the L/S ration, and technically is the most difficult.

A recent study, Reference (2), shows that the L/S ratio of tracheal and pharyngeal aspirates in newborns with severe RDS provides useful information in predicting the outcome of the disease. Based on this study, the prognosis is death within a relatively short time after birth for infants with clinical RDS whose L/S ratio is less than one. Thus, it is clear that the L/S ratio, and perhaps the bubble stability test and measurement of the lecithin concentration, are useful tools in evaluating perinatal lung maturity. Obviously, this is an area of great public interest and need, and considerable effort has been devoted to improving and to devising new techniques for this purpose.

It is therefore an object of this invention to provide a new and improved method that facilitates the evaluation of perinatal lung maturity by a faster and more accurate technique that is less complex than techniques heretofore known.

SUMMARY OF THE INVENTION

The present invention provides a method for evaluating perinatal maturity by determining the fluorescence polarization of a sample of pulmonary effluent containing pulmonary surfactant labeled with a fluorescent dye. The sample is excited with polarized radiation for causing the dye to fluoresce. The intensity of fluorescence polarized in a direction parallel to the direction of polarization of the excitation radiation, hereinafter termed $I_\parallel$, and the intensity of fluorescence polarized in a direction perpendicular to the direction of polarization of the excitation radiation, hereinafter termed $I_\perp$ are measured preferably at right angles to the excitation beam. The fluorescence polarization P is determined as follows:

$$P = (I_\parallel - I_\perp)/(I_\parallel + I_\perp) \tag{1}$$

The value of P, which is functionally related to the microviscosity of constituents of the surfactant as indicated in reference (3), has been found to decrease with perinatal lung maturity. When the sample is amniotic fluid containing pulmonary effluent, an evaluation of fetal lung maturity can be carried out antepartum. Postpartum evaluation of neonatal lung maturity can be carried out by sampling tracheal or pharyngeal aspirates.

An instrument for carrying out the invention is disclosed in U.S. Pat. No. 3,971,952 granted July 27, 1976. is hereby incorporated by reference. Reference (4) also describes this instrument.

DESCRIPTION OF PREFERRED EMBODIMENT

In the antepartum evaluation of fetal lung maturity, freshly drawn amniotic fluid is first centrifuged in order to segregate tissue fragments and cells which are discarded. To evaluate neonatal lung maturity, tracheal or pharyngeal aspirates of newborns are used. In each case, lecithin and sphingomyelin are present in the samples as a consequence of pulmonary effluent. These phospholipids are stained (i.e., labeled) with a lipid soluble dye added to the fluid.

After incubation for a period of time sufficient to stabilize the fluorescent output, the sample is excited by polarized radiation. The intensities of fluorescence polarized in directions parallel to, and perpendicular to, the direction of polarization of the excitation radiation are measured. From these measurements, the fluorescence polarization P can be determined by means of equation (1) wherein $I_\parallel$ is the intensity of fluorescence measured in a direction parallel to the direction of polarization of the excitation radiation, and $I_\perp$ is the intensity of fluorescence measured in a direction perpendicular to the direction of polarization of the excitation radiation.

The fluorescence polarization is functionally related to the mircroviscosity of the lipid dispersion in the sample. The lipids, which are mostly lecithin and sphingomyelin as indicated above, are characterized by low solubility in water, and form micelles which are colloidal-sized aggregates of molecules. The viscosity of the interior of the micelles is termed microviscosity as indicated in reference (3). Its measurement is based on fluorescence polarization analysis of a molecular probe (i.e., a fluorescent dye) embedded (i.e., dissolved) in the micelles. When excited, the probe simulates a rotating member in the micelles enabling the viscosity of the interiors thereof to be measured.

The microviscosity of the lipid dispersion in the sample is independent of the concentration of the lipids in the sample and the amount of fluorescent dye used for labeling. Consequently, these factors can vary over a wide range without significantly affecting the fluorescence polarization P. As indicated in reference (5), the microviscosity of a lecithin dispersion is markedly different from the microviscosity of a sphingomyelin dispersion. Consequently, the microviscosity of a sample containing a combination of these lipids will be the weighted average of the microviscosities of the components. This situation is reflected in the measured value of fluorescence polarization.

It has been found that the fluorescence polarization of a sample of pulmonary effluent labeled with a fluorescent dye (as well as the microviscosity of the lipid dispersion therein) provides a direct determination of the relative amount of surfactant in the sample. Generally, the fluorescence polarization decreases during gestation and increases with the severity of RDS in newborns. Consequently, this property of a sample of pulmonary effluent, or its microviscosity, provides a reliable indicator of perinatal lung maturity.

There are many different kinds of lipid soluable fluorescent dyes. Two examples are: perylene and DPH (1.6 diphenyl -1.3.5 hexatriene). Because of its high fluorescent yield, DPH is preferred even though it must be excited with U.V. light. Perylene can be excited with visible light, but its fluorescent output is weaker than DPH, so that measurements involving perylene are more sensitive to background fluorescence, a situation which may occur in any liquid of biological origin.

When the dye is perylene, the excitation radiation should be at 400-420 nm. For DPH, the excitation should be at 365 nm. In either case, the excitation radiation incident on the sample must be polarized. The intensities of fluorescence polarized in directions parallel to, and perpendicular to, the direction of polarization of the excitation radiation are measured to obtain $I_\parallel$ and $I_\perp$, preferably simultaneously along channels at right angles to the incident excitation beam.

The cell holding the sample must be transparent to the excitation radiation and the resultant fluorescent output. And since the measurements are temperature sensitive, the sample cell should be termperature stabilized. Preferably, the stabilization should be $\pm$ 1° C. Instruments having these characteristics for obtaining fluorescence polarization and/or microviscosity are disclosed in copending application Ser. No. 505,530 and in reference (4). A commercial instrument based on these disclosures is the MV-1 microviscosimeter manufactured by Elscint Ltd., Haifa, Israel which includes a computing unit that directly reads-out the value of fluorescence polarization.

When the sample is amniotic fluid, the value of fluorescence polarization at 25° C varies, typically, from 0.340 to 0.200 when the dye is DPH, and from 0.200 to 0.100 when the dye is perylene from the 22nd week to the 40th week of gestation. When the sample is tracheal or phyrangeal aspirates, the value of fluorescence polarization at 25° C would vary from greater than 0.3 to less than 0.24 depending upon the severity of RDS.

While the measurement of fluorescence polarization can be carried out at any reasonable temperature, the temperature sensitivity of P is such that at different temperatures, a different range of P values will be obtained for the same range of lipid content. Comparative measurements must therefore be made at the same temperature.

While fluorescence polarization is a commonly measured parameter of a lipid dispersion, the instrument described above actually measures $I_\parallel$ and $I_\perp$ simultaneously; and the ratio $(I_\parallel - I_\perp)/(I_\parallel + I_\perp)$ is computed and displayed. It is clear that $I_\parallel$ and $I_\perp$ could be measured, and the quantity P computed from these measurements. Other parameters for evaluating lung maturity can also be computed, namely the fluorescence anisotropy, $r$, and the total fluorescence intensity, F, given by:

$$r = (I_\parallel - I_\perp)/(I_\parallel + 2I_\perp)$$

$$F = I_\parallel + 2I_\perp$$

EXAMPLE I

1. Stock solution of DPH

A stock solution of DPH is obtained by dissolving 4.6 mg of DPH in 10 ml of THF (tetrahydrofuron) and is kept in a tightly closed bottle. The solution is stable for at least 2 months.

2. Aqueous dispersion of DPH

DPH is dispersed in an aqueous solution by injecting or blowing 0.1 ml of the stock solution of DPH into 200 ml of vigorously stirred PBS (phosphate buffered saline, ph of 7.2). The resultant dispersion should be clear and devoid of fluorescence. It should be discarded if not used within 24 hours. Preferably, the dispersion should be prepared just before it is to be used.

3. Sample preparation

Two ml of freshly drawn amniotic fluid is centrifuged to at least 200 g (or the highest speed of a clinical centrifuge) to segregate tissue fragments and cells which are discarded. If the fluid is contaminated with meconium or blood, a pinch of decolorizing celite mix is added and the solution re-centrifuged.

One ml of the resultant fluid is added to 4 ml of the DPH dispersion and the mixture incubated at 37° C for at least 20 minutes, but preferably up to one hour. After cooling to room temperature, the sample is ready for measurement.

4. Measurement

An instrument of the type described is used with the sample being placed in a U.V. transparent sample cell temperature stabilized at 25° C. The exciting radiation is a plane polarized light source at 365 nm.

The values of four consecutive measurements of fluorescence polarization of samples prepared as indicated above from amniotic fluid taken from a woman experiencing a normal pregnancy are:

| Gestation Week | P |
|---|---|
| 34 | 0.368 |
| 34-2/7 | 0.333 |
| 35-1/2 | 0.324 |
| delivery day | 0.254 |

EXAMPLE II

1. Stock Solution of DPH (same as in Example I)

2. Aqueous dispersion of DPH (same as in Example I)

3. Sample preparation

Pulmonary effluent is obtained through a suction catheter placed through an endotracheal tube in the newborn. Alternatively, oropharyngeal aspirates are obtained with a suction tube. In either case, a 5 ml syringe containing a 0.5 ml saline solution is used for suction.

The sample is prepared for measurement as indicated in Example I.

4. Measurement

The fluorescence polarization is measured as in Example I.

It is believed that the advantages and improved results furnished by the method of the invention will be apparent from the foregoing description of several preferred embodiments of the invention. Various changes and modifications may be made without departing from the spirit and scope of the invention as sought to be defined in the following claims.

We claim:

1. A method for evaluating perinatal lung maturity by determining the degree of fluorescence polarization of a sample of pulmonary effluent containing pulmonary surfactant within which a fluorescent dye is dissolved.

2. A method for evaluating perinatal lung maturity comprising:
   a. obtaining a sample of pulmonary effluent containing pulmonary surfactant;
   b. labeling the surfactant with a fluorescent dye;
   c. exciting the sample with polarized radiation for causing the sample to fluoresce; and
   d. measuring the intensities of fluorescence polarized in directions parallel to, and perpendicular to, the direction of polarization of the excitation radiation.

3. A method according to claim 2 wherein the fluorescence polarization is calculated from the polarized intensities of fluorescence.

4. A method according to claim 2 wherein the pulmonary surfactant is a nonacidic phospholipid and the dye is a lipid soluble fluorescent molecule.

5. A method according to claim 4 for evaluating fetal lung maturity wherein the sample is obtained antepartum and is contained in amniotic fluid.

6. A method according to claim 4 for evaluating neonatal lung maturity wherein the sample is obtained postpartum from tracheal or pharyngeal aspirates.

7. A method according to claim 4 wherein the dye is DPH.

8. A method according to claim 4 wherein the dye is perylene.

9. A method according to claim 7 wherein the excitation radiation is monochromatic light at 365 nm.

* * * * *